United States Patent [19]
Langkau

[11] Patent Number: 5,766,150
[45] Date of Patent: Jun. 16, 1998

[54] PROCESS FOR THE FILING OF A PROPELLANT CHAMBER OF A GAS DRIVEN PUMP

[75] Inventor: Wolfram Langkau, Steinbach, Germany

[73] Assignee: Fresenius AG, Germany

[21] Appl. No.: 644,789

[22] Filed: May 10, 1996

[30] Foreign Application Priority Data

May 11, 1995 [DE] Germany .................. 195 17 291.4

[51] Int. Cl.⁶ .................................................. A61M 11/00
[52] U.S. Cl. .................. 604/93; 604/43; 604/140; 604/141; 141/3; 141/4; 141/9; 141/65
[58] Field of Search ..................... 604/49, 93, 140, 604/141; 141/2, 3, 4, 9, 18, 20, 65, 100

[56] References Cited

U.S. PATENT DOCUMENTS

| | | | |
|---|---|---|---|
| 3,840,009 | 10/1974 | Michaels et al. | 604/892.1 |
| 4,604,090 | 8/1986 | Reinicke | 604/118 |
| 5,167,633 | 12/1992 | Mann et al. | 604/141 |
| 5,197,322 | 3/1993 | Indravudh . | |
| 5,514,103 | 5/1996 | Srisathapat et al. | 604/141 |

FOREIGN PATENT DOCUMENTS

| | | |
|---|---|---|
| 75062 A | 3/1983 | European Pat. Off. . |
| A-142866 | 5/1985 | European Pat. Off. . |
| 4333736 A | 4/1995 | Germany . |

Primary Examiner—Mark Bockelman
Assistant Examiner—Jennifer R. Sadula

[57] ABSTRACT

A process for the filling of the pumping chamber of a gas pressure driven medicine pump. A pillow filled with the propellant is formed which consists of a material permeable to the propellant. The pillow filled with the propellant is inserted into the propellant chamber which is evacuated. Then, the propellant chamber is sealed gas tight. Subsequently, the propellant diffuses through the wall of the pillow into the propellant chamber. The process according to the invention offers the possibility of filling the pumping chamber in a simple manner without allowing the penetration of foreign gases.

10 Claims, 2 Drawing Sheets

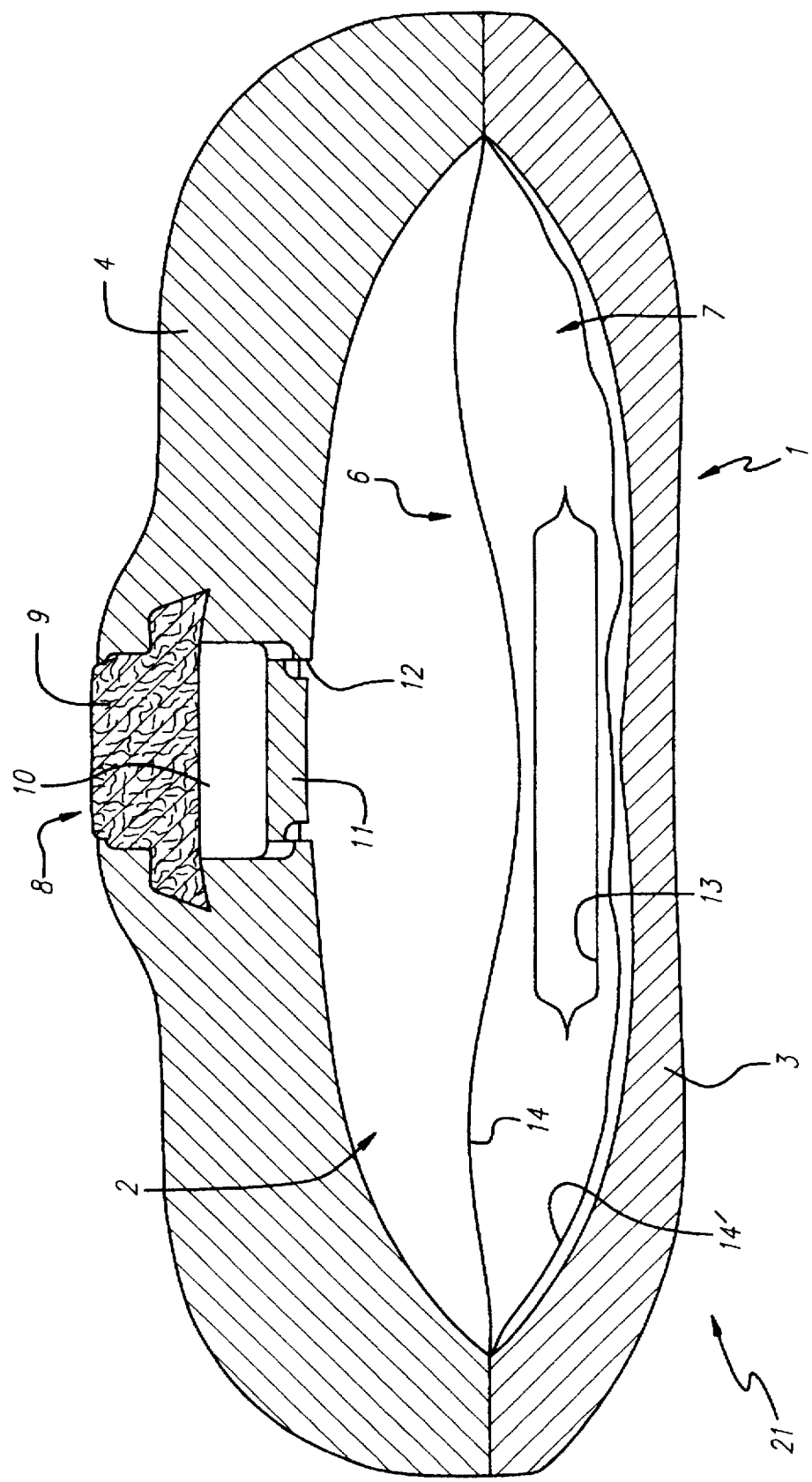

5,766,150

PROCESS FOR THE FILING OF A PROPELLANT CHAMBER OF A GAS DRIVEN PUMP

BACKGROUND OF THE INVENTION

1. Field of the Invention

The present invention relates to a process for the filling of a gas pressure driven pump for medication with a fluid propellant. It refers in particular to a process for the filling of an implanted infusion pump with propellant.

2. Description of the Prior Art

Gas pressure driven medicine pumps, in particular implantable infusion pumps are used for continuous medication (constant dosage) for relatively long periods of time in patients who otherwise could be treated only by injection of the medications, such as morphines, heparines and the like, several times daily. These pumps are advantageous in comparison with the conventional injections in that the dose administered no longer has to be overdosed to the extent that it does not fall below a certain minimal dosage by the next administration time despite the decomposition of the medication, but that a uniform flow and a significantly lower total supply of the drug can be realized.

Such a medicine pump has a pumping chamber which is divided by means of a flexible partition, e.g., a membrane or a corrugated bellows, into two subchambers, one containing the medicine and one a propellant. The mode of action in such a medicine pump is such that in operation condition the propellant contained in the pump is available in an equilibrium condition between liquid and gaseous phase. The vapor pressure of the propellant must be sufficiently above atmospheric pressure to exert pressure on the medication chamber via the separating partition, such that it releases the medicine via a reduction system against surrounding pressure into the body of the patient. The volume increase of the propellant compartment is equalized by the further evaporation of the propellant and takes place at a constant isobar, as long as the propellant is a two phase system.

Such medicine pumps are known, for example, from DE 43 33 736 and EP 0 075 062. DE 43 33 736 describes a pump whose medicine compartment is formed by a bellows. The outside of the bellows is disposed in a pressure tight can provided with a propellant exerting a constant pressure which compresses the bellows thus expelling the medicine. In contrast, EP 0 075 062 describes a pump where the propellant chamber is separated from the chamber with the active substance by means of an impermeable membrane. The pressure produced in the propellant chamber by the propellant is exerted via the membrane on the chamber containing the active substance and the active substance is thus released in constant dosage.

Different processes are known for charging the propellant chamber. EP 0 142 866 discloses a process for the filling of an implantable infusion pump. This infusion pump consists of two sections that are connected to each other only after filling with the propellant. The propellant chamber is delimited on one side by the lower partial housing, on the other side by a diaphragm. For propellant charging, a propellant mixture with a vapor pressure of 0.55 to 0.62 bar at body temperature is first prepared. The mixture is subsequently freed of dissolved air under vacuum. Next, the mixture and the propellant chamber are heated to 51.7° C. After a vacuum has been established in the propellant chamber and the external diaphragm side, the warmed propellant is introduced through a small opening in the lower partial housing into the propellant chamber and the chamber adjacent to the external diaphragm side. Then, pressure is exerted onto the external diaphragm side by air or nitrogen such that most of the propellant is ejected again from the propellant chamber. The opening in the lower partial housing is closed with a stopper and the lower partial housing connected to the upper housing part. This process, however, has the great disadvantage that it is expensive and that substantially larger amounts of propellant are required for charging than is necessary later on for the operation of the pump.

Another process is disclosed in DE-A 195 09 632 where the propellant charging of an implantable infusion pump requires no more than the amount of propellant required for the operation of the pump. The propellant chamber of this pump is formed by two deep drawn metal foils or metal film laminations which are connected to each other in the edge area of the entire circumference by means of edge glueing. A microcapillary is introduced through the sealing surface into this pill-shaped formation, through which the chamber is first evacuated and subsequently charged with propellant. The disadvantages in this procedure are, however, that the capillaries are very sensitive and break very easily, thus rendering the pump unusable. Furthermore, the sealing surface between the foils is not adequate, and foreign gases may thus enter the propellant chamber through the sealing surface.

Because of the penetration of foreign gases, however, the correct function of the infusion pump is no longer guaranteed, since the evaporation of the propellant no longer takes place under isobaric conditions. The pressure acting on the membrane decreases with the volume increase of the propellant chamber and thus diminishes the delivery rate of the medication.

It is thus the object of the invention to provide a process by which the propellant chamber of a pumping chamber of a gas pressure driven pump, in particular an implantable infusion pump, can be filled simply without foreign gases able to penetrate into the pumping chamber.

SUMMARY OF THE INVENTION

The preceding and other shortcomings of prior art are addressed and overcome by the present invention which provides a process for the filling of a propellant chamber of a gas pressure driven pump, in particular an implantable infusion pump with a fluid propellant where the pumping chamber of the gas pressure driven pump is divided into the propellant chamber and a liquid storage chamber, the propellant chamber essentially is freed of gases and filled with the fluid propellant, wherein a pillow essentially permeable to the propellant but inert is filled with the propellant and said pillow is placed in the propellant chamber and the propellant chamber is closed.

In another aspect, the present invention provides a gas pressure driven pump, in particular an implantable infusion pump with a pumping chamber which is divided into a liquid storage chamber and a propellant chamber, wherein a pillow filled with propellant is inserted into the propellant chamber which pillow is permeable to but inert to the propellant

BRIEF DESCRIPTION OF THE DRAWINGS

FIG. 2 is an illustration of a cross-section through an implantable medicine pump in schematic presentation

DETAILED DESCRIPTION OF THE PREFERRED EMBODIMENT(S)

Figure 1:
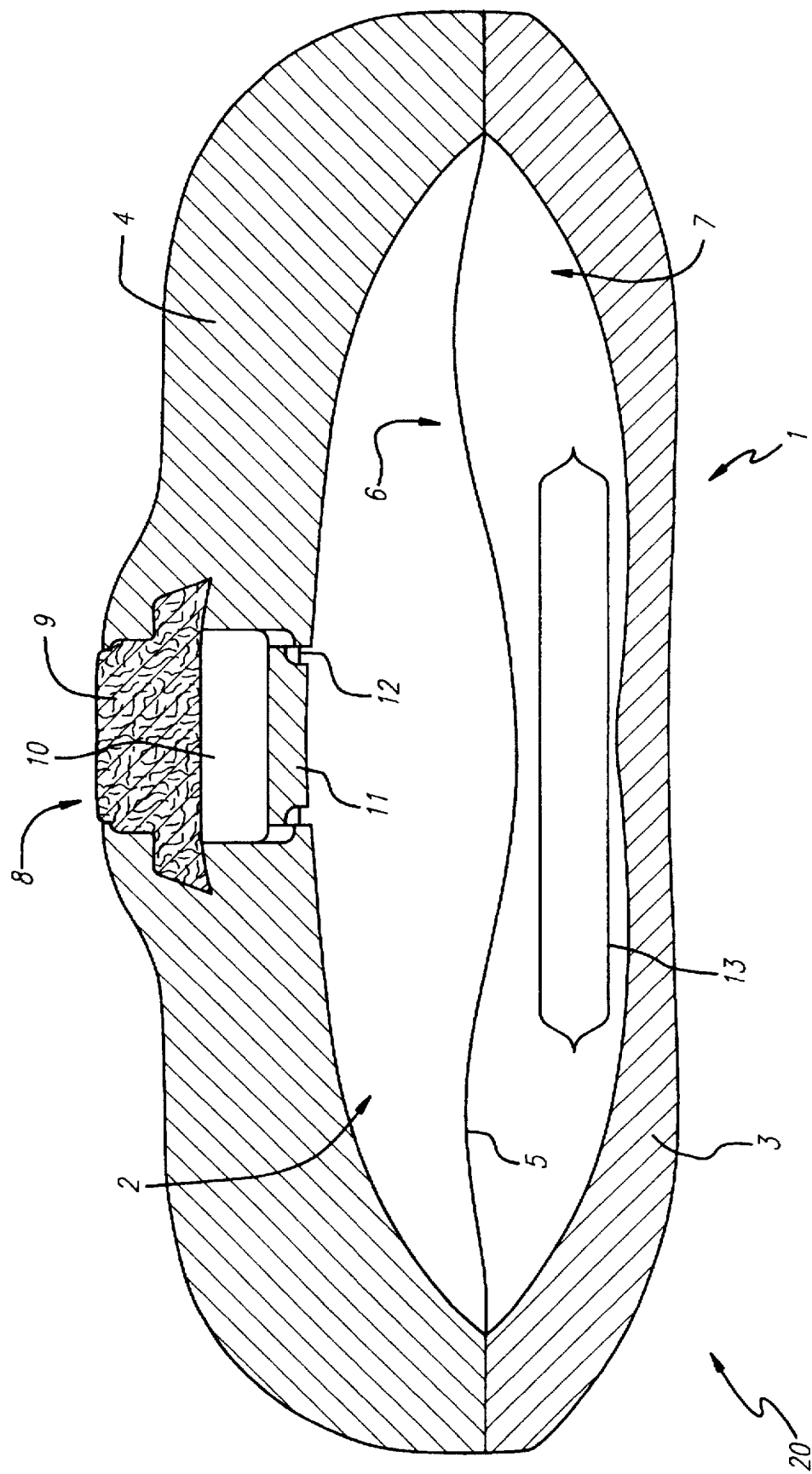
FIG. 1 is an illustration of a cross-section through an implantable medicine pump in schematic presentation whereby its pumping chamber is divided by a flexible partition into a medicine chamber and a propellant chamber whereby the propellant chamber contains a pillow filled with propellant which is permeable to the propellant.

According to the invention the propellant chamber 7 is filled with propellant whereby a pillow 13 filled with propellant is placed into the propellant chamber 7 of the pumping chamber 2 and the pumping chamber 2 evacuated. The pillow 13 preferably consists of a material through which the propellant may diffuse but which is not attacked by the propellant. Subsequently, the propellant chamber 7 is sealed gas tight. The propellant then slowly diffuses through the wall of the propellant pillow 13 to the outside. Slowly refers to the condition whereby after approximately 15 minutes the propellant is diffused to the outside through the micropores of the polymer material. The empty propellant pillow 13 remains in the propellant chamber 7. It is, however, also possible to make use of a material essentially impermeable to the propellant, which is burst by subjecting it to vacuum from the outside.

In a preferred embodiment the propellant chamber 7 of the pumping chamber 2 is formed from two deep drawn lamination foils, a metal or metal lamination film and a gas impermeable partition as disclosed in DE-A 195 09 634 to which reference is expressively made here for the purpose of disclosure. The propellant pillow 13 is placed between the two foils and the space between the two foils evacuated. The foils forming an external pillow may be used in the pumping chamber 2 together with the propellant pillow 13 such that the outside pillow delimits the propellant chamber 7. It is, however, also possible to divide the pumping chamber 2 into the chamber for the active agent and the propellant chamber 7 by a flexible partition 5 and to insert the pill-shaped formation made of deep drawn laminated films together with the propellant pillow 13 into the space of the pumping chamber 2 which is delimited by the flexible partition 5 and the walls of the housing of the pumping chamber 2. Preferably, the pill-shaped formation is applied to a foil forming the partition 5 which foil is attached to the edge of the pumping chamber 2. The foil may be jammed or glued between the housing shells of the pumping chamber 2.

Preferably, the deep drawn foils are first connected to each other along their outside edge whereby an evacuation opening between the foils remains open at the edge. Through this opening a tube is inserted by which the space between the two foils is evacuated. The opening is subsequently closed.

A particularly preferred embodiment of the invention provides that the two foils are connected by welding of the edges. The welding of the edges preferably takes place by a ultrasound welding process. This welding process is particularly suitable for the invention because it allows for welding times of less than one second. This process substantially increases the sealing action of the composite foils at the circumference.

Not more than two minutes should elapse between the filling of the pillow 13 and the propellant chamber 7 welding thus allowing for the escape of only a small amount of the propellant. Suitably the pillow 13 consists of the element of an air padding foil upon which a silicon plate is glued. The pillow 13 is evacuated and filled by means of two needles through this silicon plate.

The volume of the propellant filled in is small and may, for example, be 2 ml. The inner volume of the pressure chamber may, for example, be 40 ml. According to the invention all common propellants used in medical pumps may be used. In implantable infusion pumps preferably hexafluorobutane is used as a propellant, whereby 1.1.1.4.4.4-hexafluorobutane is particularly preferred. Implantable infusion pumps containing this propellant are described in patent application DE-A 195 09 632, which is hereby expressively referred to for the purposes of disclosure.

The above described process substantially improves the gas tightness of the propellant chamber 7 during the filling process. It is furthermore a significant advantage of this process that microcapillaries no longer have to be inserted directly into the propellant chamber 7, thus eliminating the danger of them breaking off and thus rendering the pump unusable. The rejection ratio in the manufacturing of pumps is thus substantially reduced, resulting in an increase of production quality as well as a decrease in cumulative manufacturing cost.

Two exemplary embodiments of the invention are explained in more detail with reference to the drawings.

FIG. 1 shows a cross-section through a first embodiment of an implantable infusion pump 20 in schematic representation. The infusion pump 20 has a disk-shaped rotationally symmetric housing 1 made of hard plastic with a pumping chamber 2 which consists of a shell-shaped lower chamber part 3 and a shell shaped upper chamber part 4. The pumping chamber 2 is separated by a flexible gas permeable partition 5 into a medicine chamber 6 to accommodate a medication and a propellant chamber 7 to accommodate the 1.1.1.4.4.4-hexafluorobutane used as a propellant. The partition 5 is jammed or pressed between the edge areas of the lower chamber part 3 and upper chamber part 4 with its outside edge area. The inner volume of the propellant chamber 7 is about 40 ml, the medicine chamber 6 can accommodate approx. 30 ml of the medical solution. The infusion pump 20 is suitable for the continuous dosed release of medications such as Heparin, artificial pancreatic insulin, chemotherapeutics, pain killers etc. In the center of the upper chamber part 4 an opening 8 for refilling is provided which is tightly closed by a central septum 9. Below the central septum 9 a refilling chamber 10 with a fixed plate 11 as a needle stop and inlet openings 12 to the medicine chamber 6 are disposed.

The propellant chamber 7 is filled with the propellant as follows. First, an element is punched from an air padded foil, that is a foil with a large number of air filled chambers. The element is provided with a silicon plate about 1 mm thick and dimensions of 6×9 mm which is glued to it with a rapid holding glue. By means of two needles with an external diameter of 0.4 mm, the pillow 13 is evacuated and subsequently refilled with propellant. Before the two housing halves 3, 4 of the infusion pump are put together, the pillow 13 is inserted into the lower chamber part 3. Subsequently the lower chamber part 3 and the upper chamber part 4 are connected to each other, whereby the flexible partition 5 is jammed between the two halves 3, 4 of the housing 1. The propellant contained in the pillow 13 diffuses within 15 minutes into the propellant chamber 7 through the thin wall of the pillow 13.

FIG. 2 shows an additional embodiment of the implantable infusion pump 21 in schematic representation, whereby the parts corresponding to the parts of the pump 20 according to FIG. 1 are provided with the same references. The infusion pump 21 has a disk-shaped rotationally symmetric housing 1 made of hard plastic with a pumping chamber 2 which consists of a shell-shaped lower chamber part 3 and a shell-shaped upper chamber part 4. In the center of the upper chamber part 4 an opening 8 for refilling, which is tightly closed by a central septum 9, is provided. Below the central septum 9 a refilling chamber 10 with a fixed plate 11 as a needle stop and inlet openings 12 to the medicine chamber 2 are disposed. In this embodiment the propellant chamber 7 is formed by two deep drawn foils 14, 14' which are welded to each other. The pillow 13 filled with propellant is disposed inside the pill-shaped propellant chamber 7. The propellant chamber 7 is filled with propellant as follows. First, the pillow 13 is produced. Then, the pillow 13 is placed between the deep drawn foils 14, 14' forming the pill shaped propellant chamber 7. Next, the foils 14, 14' are welded along their outer edges whereby an evacuation opening remains on the edge of the foils 14, 14'. A tube, through which the space between the two foils 14, 14' is evacuated, is guided through this opening. By means of an ultrasound welding machine and a suitable electrode, the foils 14, 14' are subsequently welded together. No more than two minutes should elapse between the filling of the pillow 13 and the welding process. The foils 14, 14' containing the pillow 13 are placed in the shell shaped lower chamber part 3 and the two halves 3, 4 of the housing are connected to each other, whereby the foils 14, 14' are jammed by their edges. The propellant in the pillow 13 now diffuses into the pill-shaped propellant chamber 7. It is furthermore possible to add an additional foil to the welded foils 14, 14' forming a partition. This partition may be jammed together with the pillow 13 between the two halves 3, 4 of the housing 1 of the infusion pump 21.

It will be appreciated by persons skilled in the art that the present invention is not limited to what has been shown and described hereinabove, nor the dimensions or sizes of the physical implementation described immediately above.

What is claimed is:

1. A process for the filling of a propellant chamber of a gas pressure driven implantable infusion pump with a fluid propellant, comprising the steps of:

dividing a pumping chamber of the gas pressure driven pump into the propellant chamber and a liquid storage chamber, evacuating the propellant chamber of substantially all gases;

filling a pillow with the propellant, wherein the pillow is essentially permeable to and inert to the propellant;

inserting the pillow filled with the propellant in the propellant chamber; and closing the propellant chamber.

2. The process according to claim 1, wherein the evacuating step is performed after the inserting step.

3. The process according to claim 1, wherein the dividing step is accomplished by means of a flexible partition between the propellant chamber and the liquid storage chamber.

4. The process according to claim 1, wherein the inserting and dividing steps further comprise the steps of:

placing the pillow filled with propellant between two deep drawn foils impermeable to the propellant;

connecting the foils to each other by their edges to thereby form an external pillow having an evacuation opening;

evacuating the air contained in the external pillow;

closing the evacuation opening to thereby form a pill-shaped propellant chamber; and placing the external pillow in the pumping chamber.

5. The process according to claim 4, further comprising the steps of:

placing at least one additional foil on the external pillow; and attaching the at least one additional foil with the external pillow to the edge of the pumping chamber.

6. The process according to claim 1, wherein the pillow filled with propellant is made from an element of an air padded foil.

7. The process according to claim 6, further comprising the steps of:

punching out an element of an air padded foil applying a silicon plate on the element of the air padded foil forming the pillow and evacuating the pillow through the silicon plate by means of two needles and simultaneously filling with propellant.

8. The process according to claim 1, wherein no more than two minutes elapses between the filling of the pillow with propellant and the closing of the propellant chamber.

9. A gas pressure driven pump, in particular an implantable infusion pump, comprising:

a pumping chamber, which is divided into a liquid storage chamber and a propellant chamber; and a pillow filled with propellant which is inserted into the propellant chamber wherein the pillow is permeable to and inert to the propellant.

10. The gas pressure driven pump according claim 9, wherein the propellant chamber is formed by an outside pillow made of deep drawn composite foils, in which the pillow filled with propellant is disposed.

* * * * *